United States Patent [19]

Böttcher et al.

[11] Patent Number: 5,767,132

[45] Date of Patent: Jun. 16, 1998

[54] PYRIDYL CHROMAN

[75] Inventors: Henning Böttcher; Ralf DeVant, both of Darmstadt; Hartmut Greiner; Gerd Bartoszyk, both of Weiterstadt, all of Germany; Jean-Jacques Berthelon; Marc Noblet, both of Lyons, France; Jean-Jacques Zeiller, Villenbonne, France; Michel Brunet, Toussieu, France

[73] Assignee: Merck Patent Gesellschaft Mit Beschrankter Haftung, Germany

[21] Appl. No.: 543,727

[22] Filed: Oct. 16, 1995

[30] Foreign Application Priority Data

Oct. 14, 1994 [EP] European Pat. Off. .............. 94116223

[51] Int. Cl.$^6$ ............................ C07D 405/12; A61K 31/44
[52] U.S. Cl. ...................... 514/337; 514/456; 514/444; 549/60; 549/404; 549/407; 546/282.1
[58] Field of Search .......................... 546/282.1; 549/60, 549/404, 407; 514/337, 456, 444

[56] References Cited

U.S. PATENT DOCUMENTS

| 5,137,901 | 8/1992 | Junge et al. | 514/373 |
| 5,318,988 | 6/1994 | Schohe-Loop et al. | 514/458 |
| 5,468,882 | 11/1995 | Schohe-Loop et al. | 549/407 |

FOREIGN PATENT DOCUMENTS

| 0 145 067 | 6/1985 | European Pat. Off. . |
| 453 | 2/1993 | European Pat. Off. . |
| 23 64 685 | 7/1975 | Germany . |
| 41 35 474 | 4/1993 | Germany . |
| 42 26 527 | 2/1994 | Germany . |
| 93/17017 | 9/1993 | WIPO . |

OTHER PUBLICATIONS

Hirose et al., Chem. Pharm. Bull., 24(11):2661–2667 (1976).
Goldenberg et al., Chimie Therapeutique, 8(3):259–270 (May/Jun. 1973).
Chem. Abstracts, 70(7):28816q (Feb. 17, 1969).
Chem. Abstracts, 94(13):103390x (Mar. 30, 1981).
Fujikura et al., Chem. Pharm. Bull., 30(11):4092–4101 (1982).
Chem. Abstracts, 86(21):150434j (May 23, 1977).
Chem. Abstracts, 72(21):109472t (May 25, 1970).
Patent Abstracts of Japan, vol. 18, No. 19 (C–1152 (Jan. 13, 1994).

*Primary Examiner*—Jane Fan
*Attorney, Agent, or Firm*—Millen, White, Zelano & Branigan, P.C.

[57] ABSTRACT

Amino(thio)ether derivatives of formula I

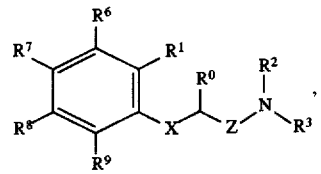

wherein $R^0$, $R^1$, $R^2$, $R^3$, $R^6$, $R^7$, $R^8$, $R^9$, X and Z are as defined herein, and their salts, are active on the central nervous system.

15 Claims, No Drawings

PYRIDYL CHROMAN

The invention relates to novel amino(thio)ether derivatives of formula I

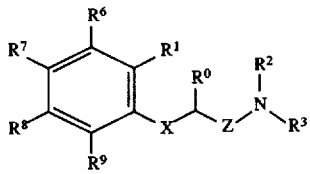

wherein

X is oxygen, sulphur, sulfinyl, sulfonyl or, in the case where $R^0$ and $R^1$ are not together an alkylene chain with 1–3 atoms, also $CH_2$, Z is —$(CH_2)_{n1}$—$(CHA)_{n2}$—$(CH_2)_{n3}$ with
n1=0, 1, 2 or 3;
n2=0 or 1;
n3=0, 1, 2 or 3 and the proviso that
n1+n2+n3<4, $R^0$ is hydrogen or A, $R^1$ is hydrogen, A, OA, phenoxy, Ph, OH, F, Cl, Br, CN, $CF_3$, COOH, COOA, acyloxy with 1–4 C atoms, carboxamido, —$CH_2NH_2$, —$CH_2NHA$, —$CH_2NA_2$, —$CH_2NHAc$, —$CH_2NHSO_2CH_3$, or $R^0$ and $R^1$ are together an alkylene chain with 1–3 C atoms or an alkenylene chain with 2–3 C atoms, $R^2$ is hydrogen, A, Ac or —$CH_2$—$R^4$, $R^3$ is —$CH_2$—R4, or —CHA—$R^4$ $R^4$ is Ph, 2-, 3- or 4-pyridyl which is unsubstituted or monosubstituted by $R^5$,or thiophene which is unsubstituted, mono- or disubstituted by A, OA, OH, F, Cl, Br, CN and/or $CF_3$, or by another thienyl group, $R^5$ is a phenyl group which is unsubstituted, or mono-, di-, tri-, tetra- or pentasubstituted by F, $CF_3$, partially or completely fluorinated A, A and/or OA, $R^6$, $R^7$, $R^8$ are independently of each other H, A, OA, phenoxy, OH, F, and $R^9$ Cl, Br, I, CN, $CF_3$, $NO_2$, $NH_2$, NHA, $NA_2$, Ac, Ph, cycloalkyl with 3–7 C atoms, —$CH_2NH_2$, —$CH_2NHA$, —$CH_2NA_2$, —$CH_2NHAc$ or —$CH_2NHSO_2CH_3$ or two adjacent residues are together an alkylene chain with 3 or 4 C atoms, and/or $R^1$ and $R^6$ are together an alkylene chain with 3 or 4 C atoms, A is alkyl with 1–6 C atoms, Ac is alkanoyl having 1–10 C atoms or aroyl having 7–11 C atoms, Ph is phenyl which is unsubstituted or substituted by $R^5$, 2-, 3- or 4-pyridyl or phenoxy, and the physiologically acceptable salts thereof.

An object of the invention is to provide novel compounds capable of being used for the preparation of drugs.

Upon further study of the specification and appended claims, further objects and advantages of this invention will become apparent to those skilled in the art.

It has been found that the compounds of formula I and their biocompatible acid addition salts possess valuable pharmacological properties. Thus, in particular, they are active on the central nervous system, especially as serotonin agonists and antagonists. They inhibit the binding of tritiated serotonin ligands to hippocampal receptors (Cossery et al., European J. Pharmacol. 140 (1987), 143–155). They also modify the accumulation of DOPA in the corpus striatum and the accumulation of 5-HTP in the nuclei raphes (Seyfried et al., European J. Pharmacol. 160 (1989), 31–41). They also have analgesic and hypotensive effects; thus, in catheterized, conscious, spontaneously hypertensive rats (strain: SHR/Okamoto/NIH-MO-CHB-Kisslegg; method: q.v. Weeks and Jones, Proc. Soc. Exptl. Biol. Med. 10 4 (1960), 646–648), the directly measured blood pressure is lowered after oral administration of the compounds. They are also useful for prophylaxis and control of the sequelae of cerebral infarction (Apoplexia cerebri) such as stroke and cerebral ischaemia.

These substances can be used in the treatment of diseases which are related to interferences in the serotoninergic and dopaminergic systems and which involve the ligands with high affinity to the 5-hydroxytryptamin (5HTIA type) or/and dopamin (D2 type) receptors.

They are suitable for the treatment of disorders of the central nervous system such as anxiety, tension and depression states, sexual dysfunctions caused by the central nervous system, disturbances in sleep or absorption of food. Furthermore, they are suitable to eliminate cognitive deficiencies, to improve powers of learning and memory and to treat Alzheimer's disease. They are also suitable for psychosis (schizophrenia).

Compounds of formula I and their biocompatible acid addition salts can therefore be used as active ingredients for anxiolytics, antidepressants, neuroleptics, and/or antihypertensives, and also as intermediates for the preparation of other pharmaceutical active ingredients.

The invention relates to the amino(thio)ether derivatives of formula I and to their biocompatible acid addition salts.

The radical A is alkyl having 1, 2, 3, 4, 5 or 6 C atoms, especially 1 or 2 C atoms, preferably methyl and also ethyl, n-propyl, isopropyl, n-butyl, isobutyl, sec-butyl or tert-butyl. OA is preferably methoxy and also ethoxy, n-propoxy, isopropoxy, n-butoxy, isobutoxy, sec-butoxy or tert-butoxy. NHA is preferably methylamino and also ethylamino, n-propylamino, isopropylamino, n-butylamino, isobutylamino, sec-butyl amino or tert-butylamino. $NA_2$ is preferably dimethylamino and also N-ethyl-N-methylamino, diethylamino, di-n-propylamino, diisopropylamino or di-n-butylamino.

Ac is preferably alkanoyl having 1–6, in particular 1, 2, 3 or 4 C atoms, in detail preferably formyl or acetyl, furthermore, preferably propionyl, butyryl, isobutyryl, pentanoyl or hexanoyl, and in addition preferably benzoyl, o-, m- or p-toluyl, 1- or 2-naphthoyl.

X is preferably oxygen or sulphur, whereas Z stands chiefly for —$CH_2$—, —$(CH_2)_2$—, —$(CH_2)_3$—, —$CHCH_3$)—, furthermore also preferably for —$CH_2$—(CHCH_3)—, —$(CH_2)_2$—$CHCH_3$)—, —$CH_2$—(CHCH_3)—$CH_2$— or —(CHCH_3)—$(CH_2)_2$—.

The residue $R^0$ is preferably H or methyl, but $R^0$ and $R^1$ are preferably together an alkylene chain, especially a chain having 2 C atoms. If $R^1$ is different from the meaning given previously it is preferably hydrogen, A, OA, $CONH_2$ or CN.

$R^2$ is preferably H or A and $R^3$ is preferably 2-, 3- or 4-pyridylmethyl or phenyl which is substituted by another phenyl or furthermore, $R^3$ is thienyl which is preferably substituted by another thienyl group.

The meaning of R3 is chiefly 2-, 3-, 4-pyridylmethyl, 5-phenyl-3-pyridylmethyl, 5-(fluorophenyl)-3-pyridylmethyl, 5-methoxyphenyl)-3-pyridylmethyl, 4'-fluoro-3-biphenylmethyl, 3-biphenylmethyl or 4-(thienyl)-2-thienylmethyl. Furthermore, the meaning of $R^3$ is preferably 2-, 4-, 5- or 6-(q -fluorophenyl)-3-pyridylmethyl, 3-, 4-, 5- or 6-(q,-fluorophenyl)-2-pyridyl methyl or 2- or 3-(q -fluorophenyl)-4-pyridyl methyl whereby q stands for the prefixes mono-, di-, tri-, tetra- or penta-.

$R^6$, $R^7$, $R^8$ and $R^9$ are preferably independently of each other H, A, OA, Cl, CN or $CF_3$. Furthermore, $R^1$ and $R^6$ are preferably together an alkylene chain with 4 C atoms. Furthermore, another preferred meaning is that two adjacent residues selected from $R^6$, $R^7$, $R^8$ and $R^9$ are together an alkylene chain with 3 or 4 C atoms.

Accordingly, the invention relates particularly to those compounds of formula I in which at least one of said radicals has one of the meanings indicated above, especially one of the preferred meanings indicated above. Some preferred groups of compounds can be expressed by the following partial formulae Ia to Ii, which correspond to formula I and in which the radicals and parameters not described in greater detail are as defined for formula I, but in which:

in Ia, X is oxygen, $R^0$ and $R^1$ are together —$(CH_2)_2$—, Z is methylene and $R^6$, $R^7$, $R^8$ and $R^9$ are hydrogen;

in Ib, X is oxygen, $R^0$ and $R^1$ are together —$(CH_2)_2$—, Z is methylene and $R^4$ is pyridyl or biphenyl which is unsubstituted or monosubstituted;

in Ic, X is oxygen, $R^0$ and $R^1$ are together —$(CH_2)_2$—, Z is methylene and $R^4$ is 5-(4-fluorophenyl)-3-pyridyl;

in Id, X is oxygen, $R^0$ and $R^1$ are together methylene and $R^4$ is 5-(4-fluorophenyl)-3-pyridyl;

in Ie, X is oxygen, $R^0$ is hydrogen, Z is methylene and $R^4$ is 5-(4-fluorophenyl)-3-pyridyl;

in If, X is oxygen, $R^0$ and $R^1$ are hydrogen, Z is methylene and $R^4$ is 5-(4-fluorophenyl)-3-pyridyl;

in Ig, X is oxygen, $R^0$ is hydrogen, $R^1$ is chlorine, ethyl or methoxy, Z is methylene and $R^4$ is 4-(4-fluorophenyl)-3-pyridyl;

in Ih, X is oxygen, Z is methylene and $R^4$ is 5-phenyl-3-pyridyl;

in Ii, X is oxygen, Z is —$(CH_2)_2$—, —$(CH_2)_3$— or —$(CHCH_3)$— and $R^4$ is 5-(4-fluorophenyl)-3-pyridyl, and the salts thereof.

Especially preferred compounds are those of partial formulae Ik and Iak to Iik, which correspond to partial formulae I and Ia to Ii, but in which additionally:

X is sulphur, sulfinyl or sulfonyl.

The invention further relates to a process for the preparation of derivatives of formula I and their salts, characterized in that a compound of formula II

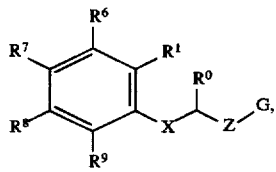

wherein

G is Cl, Br, I, OH or an OH group functionally modified to form a reactive group, especially a suitable leaving group, and $R^0$, $R^1$, $R^6$, $R^7$, $R^8$, $R^9$, X and Z are as defined, is reacted with an amine of formula III

 III.

wherein $R^2$ and $R^3$ are as defined, or in that a compound of the formula IV

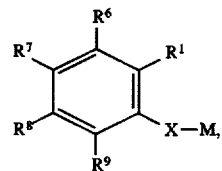 IV wherein,

M is H, Li+, Na+, K+, $NH_4$+ or another suitable metal ion, and X, $R^1$, $R^6$, $R^7$, $R^8$ and $R^9$ are as defined, is reacted with a compound of formula V

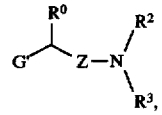 V wherein

G' has the definitions given for G and $R^0$, $R^2$, $R^3$ and Z are as defined, or in that a compound of formula VI

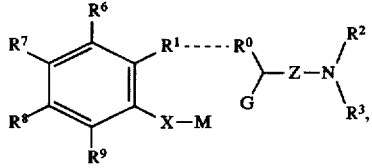 VI wherein $R^0$ and $R^1$ are together an alkylene chain with 1-3 C atoms, and $R^2$, $R^3$, $R^6$, $R^7$, $R^8$, $R^9$, X, Z, M and G are as already defined, is cyclicised to an aminoether or aminothioether derivative of formula I, or in that a compound which has formula I except that one or more hydrogen atoms have been replaced by one or more reducible groups and/or one or more additional C—C and/or C—N bonds is treated with a reducing agent, or in that a compound which has formula I except that one or more hydrogen atoms have been replaced by one or more solvolyzable groups is treated with a solvolyzing agent, and/or in that an OA group is optionally cleaved to form an OH group, and/or an Ar group is converted into another Ar group, and/or in that a resulting base or acid of formula I is converted into one of its salts by treatment with an acid or base.

The compounds of formula I are otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compounds of formula I.

In the derivatives of formula 11, G is preferably Cl or Br, but it can also be I, OH or an OH group functionally modified to form a reactive group, especially alkylsulphonyloxy having 1–6 C atoms (e.g. methanesulphonyloxy) or arylsulphonyloxy having 6–10 C atoms (e.g.

benzenesulphonyloxy, p-toluenesulphonyloxy, naphthalene-1 - or -2-sulphonyloxy).

Some of the compounds of formulae II and, in particular, III are known; the unknown compounds of formulae II and III can easily be prepared analogously to the known compounds.

Primary alcohols of the formula II can be obtained e.g. by reducing the appropriate carboxylic acids or their esters. Treatment with thionyl chloride, hydrogen bromide, phosphorus tribromide or similar halogen compounds yields the corresponding halides of the compounds of the formula II. The corresponding sulphonyloxy compounds can be obtained from the alcohols of formula II by reaction with the appropriate sulphonyl chlorides.

The iodine compounds of the formula II can be obtained, e.g., by reacting potassium iodide with the appropriate p-toluenesulphonic acid esters.

Most of the amine derivatives of formula III are known and can be obtained, e.g., by alkylation of acylation of known amines.

The reaction of the compounds of formulae II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons such as benzene, toluene or xylene; ketones such as acetone or butanone; alcohols such as methanol, ethanol, isopropanol or n-butanol; ethers such as tetrahydrofuran (THF) or dioxane; amides such as dimethylformamide (DMF) or N-methyl-pyrrolidone; or nitrites such as acetonitrile, or else, if desired, mixtures of these solvents with one another or mixtures with water. It can be favourable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of the amine component. The reaction time is between a few minutes and 14 days depending on the conditions used, and the reaction temperature is preferably about 0°–150°, normally 20°–130°.

It is also possible to obtain a compound of formula I by reacting a compound of formula IV with a compound of formula G'(CHR⁰)—Z—NR²R³ (V).

Some of the compounds of formulae V and, in particular, IV are known; the unknown compounds can easily be prepared analogously to the known compounds. Thus, compounds of formula IV can easily be prepared by metalation of a phenol or thiophenol with for example hydrides such as NaH, KH, or with phenyllithium or methyllithium. It is also possible to obtain compounds of formula IV by the oxidation of thiophenols to yield sulfinyl or sulfonyl-compounds.

The amines of formula V can be prepared starting from a primary amine by means of the diverse possibilities of alkylation or acylation of amines known per se. It is also possible to convert appropriately substituted nitro compounds into the amines of formula V by reduction and subsequent alkylation.

The reaction of compounds of formulae IV and V proceeds according to methods which are known from the literature for the formation of ethers, thioethers or esters. The components can be melted with one another directly, without the presence of a solvent, if appropriate in a closed tube or in an autoclave, at normal pressure or at elevated pressure, an inert gas such as, e.g., $N_2$ being added to increase the pressure. However, it is also possible to react the compounds in the presence of an inert solvent. Suitable solvents are those mentioned previously for the reaction of compounds of formula II with those of formula III. The addition of an acid-binding agent to the reaction mixture can also have a favorable effect. The same bases are suitable as those previously described for the reaction of compounds of formulae II and III.

Depending on the reaction conditions chosen, the optimum reaction time is between a few minutes and 14 days, and the reaction temperature is preferably about 0°–150°, usually 20°–130°.

Furthermore, a compound of formula I can be obtained by cyclization of a compound of formula VI wherein $R^0$ and $R^1$ are together an alkylene chain with 1 to 3 C atoms.

Compounds of the formula VI can be obtained, for example, by the reduction of ketones which are similar to compounds of formula VI but wherein the CHG-group is replaced by a carbonyl group.

The cyclization reaction of a compound of the formula VI proceeds according to the methods described previously for the reaction of the compounds of formulae IV and V under equal reaction conditions.

A compound of formula I can also be obtained by treating a precursor, in which hydrogen atoms have been replaced by one or more reducible groups and/or one or more additional C—C and/or C—N bonds, with a reducing agent, preferably at temperatures of about –80° to +250°, in the presence of at least one inert solvent.

Reducible groups (groups replaceable by hydrogen) are, in particular, oxygen in a carbonyl group, hydroxyl, arylsulphonyl (e.g., p-toluenesulphonyloxy), N-benzenesulphonyl, N-benzyl or O-benzyl.

In principle, compounds containing only one of the above-mentioned groups or additional bonds, or compounds containing two or more of the above-mentioned groups or additional bonds adjacent to one another, can be converted into a compound of formula I by reduction, it being possible simultaneously to reduce substituents which are present in the starting compound. This is, for example, carried out using nascent hydrogen or complex metal hydrides or by means of a Wolff-Kishner reduction or the reductions with hydrogen gas under transition metal catalysis.

Preferred starting materials for the reduction have formula VII

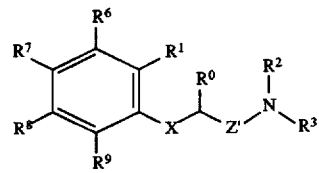

wherein

Z' is a chain which corresponds to the radical Z except that one or more —CH₂ groups have been replaced by —CO— and/or one or more hydrogen atoms have been replaced by Cl, Br, F, SH, or OH groups.

Compounds of formula VII can be obtained by amidation of acids, acid halides, anhydrides or esters with primary or secondary amines. It is preferred to react the free carboxylic acid with the amine under the conditions of a peptide synthesis. This reaction is preferably carried out in the presence of a dehydrating agent, e.g. a carbodiimide such as dicyclohexylcarbodiimide or else N-(3-dimethylaminopropyl)-N-ethylcarbodiimide, or propanephosphonic anhydride (q.v. Angew. Chem. 92, 129 (1980)), diphenylphosphoryl azide or 2-ethoxy-N-ethoxycarbonyl-1, 2-dihydroquinoline, in an inert solvent e.g a halogenated hydrocarbon such as methylene chloride, an ether such as THF or dioxane, an amide such as DMF or dimethylacetamide, or a nitrile such as acetonitrile, at temperatures of preferably about −10°–40°, especially 0°–30°.

If nascent hydrogen is used as the reducing agent, this can be produced e.g. by treating metals with weak acids or with bases. Thus it is possible e.g to use a mixture of zinc with an alkali metal hydroxide solution or a mixture of iron with acetic acid. It is also appropriate to use sodium or another alkali metal in an alcohol such as ethanol, isopropanol, butanol, amyl or isoamyl alcohol or phenol. It is also possible to use an aluminium-nickel alloy in aqueous-alkaline solution, ethanol being added if necessary. Sodium amalgam or aluminium amalgam in aqueous-alcoholic or aqueous solution is also suitable for producing the nascent hydrogen. The reaction can also be carried out in the heterogeneous phase, in which case it is convenient to use an aqueous phase and a benzene or toluene phase.

Other reducing agents which can be used to particular advantage a complex metal hydrides such as $LiAlH_4$, $NaBH_4$, diisobutylaluminium hydride or $NaAl(OCH_2CH_2OCH_3)_2H_2$, and diborane, catalysts such as $BF_3$, $AlCl_3$ or $LiBr$ being added if desired. Solvents which are suitable for this purpose are, in particular, ethers such as diethyl ether, di-ri-butyl ether, THF, dioxane, diglyme or 1,2-dimethoxyethane, and hydrocarbons such as benzene. Solvents which are suitable for a reduction with $NaBH_4$ are primarily alcohols such as methanol or ethanol, as well as water and aqueous alcohols. Reduction by these methods is preferably carried out at temperatures of preferably about −80° to +150°, especially about 0°–100°.

The reduction of —CO groups in acid amides (e.g. those of formula VI in which Z' is a —$(CH_2)_{n1}(CHA)_{n2}$—CO group) to $CH_2$ groups can be carried out to particular advantage with $LiAlH_4$ in THF at temperatures of preferably about 0°–66.

It is also possible to reduce one or more carbonyl groups to $CH_2$ groups according to the Wolff-Kishner method, e.g. by treatment with anhydrous hydrazine in absolute ethanol, under pressure, at temperatures of preferably about 150°–250°. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 34 hours. The water is then distilled off and the hydrazone formed is decomposed at temperatures of up to about 200°. The Wolff-Kishner reduction can also be carried out with hydrazine in dimethyl sulphoxide at room temperature.

Moreover, it is possible to carry out certain reductions by using $H_2$ gas under the catalytic action of transition metals, such as e.g. Raney Ni or Pd. In this way, e.g. Cl, Br, I, SH or, in certain cases, even OH groups can be replaced by hydrogen. Nitro groups can also be converted into $NH_2$ groups by catalytic hydrogenation with $Pd/H_2$ in methanol.

Compounds which have formula I except that one or more H atoms have been replaced by one or more solvolyzable groups can be solvolyzed, especially hydrolyzed, to give the compounds of formula I.

The starting materials for the solvolysis can be obtained, for example, by reacting compounds of formula III with compounds which have formula II except that one or more H atoms have been replaced by one or more solvolyzable groups. Thus, in particular, 1-acylamine derivatives (which have formula I except that, in the 1-position of the radical, they contain an acyl group, preferably an alkanoyl, alkylsulphonyl or arylsulphonyl group having up to 10 C atoms in each case, such as methanesulphonyl, benzenesulphonyl or p-toluenesulphonyl) can be hydrolyzed to give the corresponding secondary amine derivatives, e.g., in an acidic or, preferably, neutral or alkaline medium at temperatures of preferably about 0°–200°. Sodium, potassium or calcium hydroxide, sodium or potassium carbonate, or ammonia, is conveniently used as the base. The chosen solvents are preferably water; lower alcohols such as methanol or ethanol; ethers such as THF or dioxane; sulphones such as tetramethylene sulphone; or mixtures thereof, especially mixtures containing water. Hydrolysis can also be carried out simply by treatment with water alone, especially at the boiling point.

A compound of formula I can furthermore be converted to another compound of formula I by methods known per se.

Compounds of formula I in which for example $R^2$ is hydrogen can be converted to compounds with tertiary amino groups by alkylation or acylation of the secondary amino residue in an inert solvent, e.g. a halogenated hydrocarbon such as methylene chloride, an ether such as THF or dioxane, an amide such as DMF or dimethylacetamide, or a nitrile such as acetonitrile, at temperatures of about −10 to the boiling point of the solvent, preferably 0°–70°. Furthermore, other primary amino groups can be transformed to secondary or tertiary amino groups by the known alkylation reactions.

Compounds of formula I can also be converted into other derivatives of formula I by transformations at the radical Ar.

Ethers of formula I in which the radical Ph is mono- or disubstituted by O-alkyl can be cleaved, the corresponding hydroxy derivatives being formed. It is possible, e.g. to cleave the ethers by treatment with dimethyl sulphide-boron tribromide complex, for example in toluene, ethers such as THF or dimethyl sulphoxide, or by melting with pyridine or aniline hydrohalides, preferably pyridine hydrochloride, at about 150°–250°.

If other side reactions in the compounds of formula I are to be excluded, the radicals Ph can be chlorinated, brominated or alkylated under the conditions of the Friedel-Crafts-reactions, by reacting the appropriate halogen or alkyl chloride or alkyl bromide under the catalysis of Lewis acids, such as, e.g., $AlCl_3$, $FeBr_3$ or Fe, at temperatures of about 30°–150°, expediently 50°–150° in an inert solvent, such as, e.g., hydrocarbons, THF or carbon tetrachloride, with the compound of the formula I to be derivatised. Moreover, it is for example possible to reduce a nitro group to an amino group by the reactions known per se.

The compounds of formula I can possess one or more centres of asymmetry. When prepared, they can therefore be obtained as racemates or else in the optically active form if optically active starting materials are used. When synthesized, compounds possessing two or more centres of asymmetry are generally obtained as mixtures of racemates, from which the individual racemates can be isolated in the pure form, for example by recrystallization from inert solvents. If desired, the racemates obtained can be chemically or by crystallization of conglomerates resolved into their optical antipodes by the methods known per se. Preferably, diastereoisomers are formed from the racemate by reaction with an optically active resolving agent. Examples of suitable resolving agents are optically active acids such as the D and L forms of protected amino acid derivatives such as tosylproline, tartaric acid, dibenzoyltartaric acid, diacetyltartaric acid, camphor-sulphonic acids, mandelic acid, malic acid or lactic acid. The different forms of the diastereoisomers can be resolved in a manner known per se, e.g. by fractional crystallization, and the optically active compounds of formula I can be liberated from the diastereoisomers in a manner known per se.

A base of formula I can be converted with an acid into the corresponding acid addition salt. Acids which produce biocompatible salts are suitable for this reaction. Thus it is possible to use inorganic acids, e.g. sulphuric acid, hydrohalic acids such as hydrochloric acid or hydrobromic acid, phosphoric acids such as orthophosphoric acid, nitric acid and sulphamic acid, as well as organic acids, i. e. specifically aliphatic, alicyclic, araliphatic, aromatic or heterocyclic monobasic or polybasic carboxylic, sulphonic or sulphuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulphonic or ethanesulphonic acid, ethanedisulphonic acid, 2-hydroxyethanesulphonic acid, benzenesulphonic acid, p-toluenesulphonic acid, naphthalenemonosulphonic and naphthalenedisulphonic acids and laurylsulphuric acid.

If desired, the free bases of formula I can be liberated from their salts by treatment with strong bases such as sodium or potassium hydroxide or sodium or potassium carbonate provided there are no other acid group in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of formula I and their biocompatible salts for the manufacture of pharmaceutical preparations, especially by a non-chemical route. For this purpose, they can be converted into a suitable dosage form together with at least one excipient or adjunct and, if appropriate; in combination with one or more additional active ingredients.

The invention further relates to compositions, especially pharmaceutical preparations, containing at least one compound of formula I and/or one of their biocompatible salts. These preparations can be used as drugs in human or veterinary medicine. Possible excipients are organic or inorganic substances which are suitable for enteral (e.g. oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used e.g. to manufacture injectable preparations.

The preparations indicated can be sterilized and/or can contain adjuncts such as lubricants, preservatives, stabilizers and/or wetting agents, emulsifiers, salts for influencing the osmotic pressure, buffer substances, colourants, taste correctors and/or flavourings. If desired, they can also contain one or more additional active ingredients, e.g. one or more vitamins.

The compounds of formula I and their biocompatible salts can be used for the therapeutic treatment of the human or animal body and for controlling diseases. They can be used for treating disorders of the central nervous system, such as tension, depressions and/or psychoses, and side-effects in the treatment of hypertension (e.g. with a-methyldopa). The compounds can also be used in endocrinology and gynaecology, e.g. for the therapeutic treatment of acromegaly, hypogonadism, secondary amenorrhoea, premenstrual syndrome and undesired puerperal lactation, and also for the prophylaxis and therapy of cerebral disorders (e.g. migraine), especially in geriatrics in a manner similar to certain ergot alkaloids and for controlling the sequelae of cerebral infarction (Apoplexia cerebri), such as stroke and cerebral ischaemia.

Furthermore, they are suitable to eliminate cognitive deficiencies, to improve the power of learning and memory and to treat Alzheimer disease.

In these treatments, the substances of formula I of the invention are normally administered analogously to known, commercially available preparations (e.g. bromocriptine, dihydroergocomin), preferably in dosages of about 0.2–500 mg, especially about 0.2–50 mg per dosage unit. The daily dosage is preferably about 0.001–10 mg/kg of body weight. The low dosages (about 0.2–1 mg per dosage unit; about 0.001–0.005 mg/kg of body weight) are particularly suitable for use as anti-migraine preparations; dosages of about 10–50 mg per dosage unit are preferred for the other indications. However, the particular dose for each individual patient depends on a very wide variety of factors, for example, the activity of the particular compound used, age, body weight, general state of health, sex, diet, time and method of administration, rate of excretion, drug combination and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding European application 94116223.2, are hereby incorporated by reference.

EXAMPLES

In the following Examples, "working-up in conventional manner" means: Water is added if necessary, extraction is carried out with methylene chloride, the organic phase is separated off, dried over sodium sulphate and filtered, the filtrate is evaporated and the residue is purified by chromatography on silica gel and/or by crystallization. Temperatures are given in °C.

Example 1

A solution of 2.8 g 2-aminomethyl-chromane [obtainable by reacting 3-(2-hydroxy-phenyl)-propanal with KCN and subsequent catalytic reduction of the 2-cyano-chromane] and 2.2 g 3-chloromethyl)-pyridine in 250 ml of DMF are stirred together with 1 g N-methyl-morpholine for 12 hours at 20° and worked up in a conventional manner to give N-(3-pyridylmethyl)-N-(2-chromanyl-methyl)-amine. Stirring with 0.5 equivalents of maleic acid in 100 ml ethanol gives the maleate, m.p 163°–164°.

The following are obtained analogously:

from 2-aminomethyl-chromane and 3-chloromethyl)-5-(4-methoxyphenyl)-pyridine

N-[5-(4-methoxyphenyl)-3-pyridylmethyl]-N-(2-chromanyl-methyl)-amine, maleate, m.p. 177°–178°;

from 2-aminomethyl-chromane and 3-(chloromethyl)-5-phenyl-pyridine

N-(5-phenyl-3-pyridylmethyl)-N-(2-chromanyl-methyl)-amine, maleate, m.p. 184°;

from 2-aminoethyl-chromane and 3-(chloromethyl)-biphenyl

N-3-biphenylmethyl-N-(2-chromanylethyl)-amine, maleate, m.p. 162°;

from 2-aminomethyl6-phenyl-chromane and 3-(chloromethyl)-5-(4-fluorophenyl)-pyridine N-[5-(4-fluorophenyl)-3-pyridylmethyl]-N-(6-phenyl-2-chromanylmethyl)-amine, maleate, m.p. 222°–224;

from 2-aminomethyl-chromane and 3-chloromethyl)-5-4-fluorophenyl)-pyridine

N-[5(-4-fluorophenyl)-3-pyridylmethyl]-N-(2-chromanyl-methyl)-amine, maleate, m.p. 182°–183°;

from 2-aminomethyl-chromane and 3-(chloromethyl)-biphenyl

N-3-biphenylmethyl-N-(2-chromanyl-methyl)-amine, maleate, m.p. 174°–175°;

from 2-aminomethyl-chromane and 3-(chloromethyl)-4'-fluorobiphenyl

N-(4'-fluoro-3biphenylmethyl)-N-(2-chromanyl-methyl)-amine, maleate, m.p. 183°–184°;

from 2-aminomethyl-8-methoxy-chromane and 3-(chloromethyl)-5-(4-fluorophenyl)-pyridine N-[5-(4-fluorophenyl)-3-pyridylmethyl]-N-[(8-methoxy-2-chromanyl)-methyl]-amine, maleate, m.p. 160°–165°;

from 2-aminomethyl-7-methoxy-chromane and 3-(chloromethyl)-5-(4-fluorophenyl)-pyridine N-[5-(4-fluorophenyl)-3-pyridylmethyl]-N-[(7-methoxy-2-chromanyl)-methyl]-amine, maleate, m.p. 170.5°–172°;

from 2-aminomethyl6-methoxy-chromane and 3-(chloromethyl)-5-(4-fluorophenyl)-pyridine N-[5-(4-fluorophenyl)-3-pyridylmethyl]-N-[(6-methoxy-chroman-2-yl)-methyl]-amine, maleate;

from 2-aminomethyl-5-methoxy-chromane and 3-(chloromethyl)-5-(4-fluorophenyl)-pyridine N-[5-(4-fluorophenyl)-3-pyridylmethyl]-N-[(5-methoxy-chroman-2-yl)-methyl]-amine, maleate, m.p. 181°–183°;

from 2-aminomethyl-8-nitro-chromane and 3-(chloromethyl)-5-(4-fluorophenyl)-pyridine N-[5-4-fluorophenyl)-3-pyridylmethyl]-N-[(8-nitro-chroman-2-yl)-methyl]-amine, maleate;

from 2-aminomethyl-2,3,4,5-tetrahydro-1-benzoxepine and 3-(chloro-methyl)-5-(4-fluorophenyl)-pyridine N-[5-(4-fluorophenyl)-3-pyridylmethyl]-N-[2-(2,3,4,5-tetrahydro-1-benzoxepinyl)-methyl]-amine, maleate, m.p. 194°–195°;

from 2-aminoethyl-chromane and 3-(chloromethyl)-5-(4-fluorophenyl)-pyridine

N-[5-(4-fluorophenyl)-3-pyridylmethyl]-N-(2-chromanylethyl)-amine, maleate, m.p. 160°;

from 3-amino-2,3,4,5-tetrahydro-1-benzoxepine and 3-(chloromethyl)-5-(4-fluorophenyl)-pyridine N-[5-(4-fluorophenyl)-3-pyridylmethyl]-N-3-(2,3,4,5-tetrahydro-1-benzoxepinyl)-amine, maleate, m.p. 179°–180°;

from 2-aminomethyl-8-hydroxy-chromane and 3-(chloromethyl)-5-(4-fluorophenyl)-pyridine N-[5-(4-fluorophenyl)-3-pyridylmethyl]-N-[(8-hydroxy-2-chromanyl)-methyl]-amine, maleate, m.p. 173°;

from 2-aminomethyl-8-methoxy-chromane and 3-(chloromethyl)-4'-fluorobiphenyl

N-(4'-fluoro-3-biphenylylmethyl)-N-[(8-methoxy-2-chromanyl)-methyl]-amine, maleate, m.p. 176°;

from 2-aminomethyl-6-fluorochromane and 3-(chloromethyl)-5-(4-fluorophenyl)-pyridine N-[5-(4-fluorophenyl)-3-pyridylmethyl]-N-[(6-fluoro-2-chromanyl)-methyl]-amine, maleate, m.p. 169°–170°;

from 2-aminomethyl-chromane and 3-(2-pyridyl)-chloromethyl-benzene

N-[3-(2-pyridyl)-phenylmethyl]-N-2-chromanyl-methyl-amine, maleate, m.p. 201°;

from 2-aminomethyl-chromane and 3-(3-pyridyl)-chloromethyl-benzene

N-[3-(3-pyridyl)-phenylmethyl]-N-2-chromanyl-methyl-amine, dimaleate, m.p. 120°;

from 2-aminomethyl-8-methoxy-chromane and 3-(3-pyridyl)-chloromethyl-benzene

N-[3-(3-pyridyl)-phenylmethyl]-N-[(8-methoxy-2-chromanyl)-methyl]-amine, maleate, m.p. 85°;

from 2-aminomethyl-8-methoxy-chromane and 3-(2-pyridyl)-(chloromethyl-benzene

N-[3-(2-pyridyl)-phenylmethyl]-N-[(8-methoxy-2chromanyl)-methyl]-amine, maleate, m.p. 167°.

The following are obtained analogously (in some of the cases instead of maleic acid the compounds were treated with 0.1 n HC. solution to give the hydrochlorides):

from 2-aminomethyl-chromane and 3-(chloromethyl)-4'-methyl-biphenyl

N-(4'-methyl-3-biphenylylmethyl)-N-2-chromanyl-methyl-amine, hydrochloride, m.p. 206°–207°;

from 2-aminomethyl-chromane and 3-(chloromethyl)-4'-methoxy-biphenyl

N-(4'-methoxy-3-biphenylylmethyl)-N-2-chromanyl-methyl-amine, hydrochloride, m.p. 191°–192°;

from 2-aminomethyl-chromane and 3-(chloromethyl)-4'-trifluoromethyl-biphenyl

N-(4'-trifluoromethyl-3-biphenylylmethyl)-N-2-chromanyl-methyl-amine, hydrochloride, m.p. 181°–182°;

from 2-aminomethyl-chromane and 3-)chloromethyl)-3'-trifluoromethyl-biphenyl

N-(3'-trifluoromethyl-3-biphenylylmethyl)-N-2-chromanyl-methyl-amine, hydrochloride, m.p. 161°–162;

from 2-aminomethyl-8-methoxy-chromane and 3-(chloromethyl)-4'-trifluoromethyl-biphenyl N-(4'-trifluoromethyl-3-biphenylylmethyl)-N-[(8-methoxy-2-chromanyl)-methyl]-amine, hydrochloride, m.p. 206°–207°;

from 2-aminomethyl-8-methoxy-chromane and 3-(chloromethyl)-3'-trifluoromethyl-biphenyl N-(3'-trifluoromethyl-3-biphenylylmethyl)-N-[(8-methoxy-2-chromanyl)-methyl]-amine, hydrochloride, m.p. 206°;

from 2-aminomethyl-8-methoxy-chromane and 3-(chloromethyl)4'-methyl-biphenyl

N-(4'-methyl-3-biphenylylmethyl)-N-[(8-methoxy-2-chromanyl)-methyl]-amine, hydrochloride, m.p. 188°–189°;

from 2-aminomethyl-8-methoxy-chromane and 3-(chloromethyl)-4'-methoxy-biphenyl

N-(4'-methoxy-3-biphenylylmethyl)-N-[(8-methoxy-2-chromanyl)-methyl]-amine, hydrochloride, m.p. 186°–187°;

from 2-aminomethyl-8-methoxy-chromane and 3-(chloromethyl)-biphenyl

N-(3-biphenylylmethyl)-N-[(8-methoxy-2-chromanyl)-methyl]-amine, hydrochloride, m.p 211°–212°.

from 2-aminomethyl-6-nitro-chromane and 3-(chloromethyl)-5-(4-fluoro-phenyl)-pyridine N-[5-(4-fluorophenyl)-3-pyridylmethyl]-N-[(6-nitro-chroman-2-yl)-methyl]-amine, maleate;

from 2-aminomethyl-7-nitro-chromane and 3-(chloromethyl)-5-(4-fluoro-phenyl)-pyridine N-[5-(4-fluorophenyl)-3-pyridylmethyl]-N-[(7-nitro-chroman-2-yl)-methyl]-amine, maleate;

from 2-aminomethyl-8-chloro-chromane and 3-(chloromethyl)-5-(4-fluoro-phenyl)-pyridine N-[5-(4-fluorophenyl)-3-pyridylmethyl]-N-[(8-chloro-chroman-2-yl)-methyl]-amine, maleate;

from 2-aminomethyl-6chloro-chromane and 3-(chloromethyl)-5-(4-fluoro-phenyl)-pyridine N-[5-(4-fluorophenyl)-3-pyridylmethyl]-N-[(6-chloro-chroman-2-yl)-methyl]-amine, m.p. 78°–80°;

from 2-aminomethyl-7-chloro-chromane and 3-(chloromethyl)-5-(4-fluoro-phenyl)-pyridine N-[5-(4-fluorophenyl)-3-pyridylmethyl]-N-[(7-chloro-chroman-2-yl)-methyl]-amine, maleate;

from 2-aminomethyl-8-cyano-chromane and 3-(chloromethyl)-5-(4-fluoro-phenyl)-pyridine N-[5-(4-fluorophenyl)-3-pyridylmethyl]-N-[(8-cyano-chroman-2-yl)-methyl]-amine, maleate;

from 2-aminomethyl-6-cyano-chromane and 3-(chloromethyl)-5-(4-fluoro-phenyl)-pyridine N-[5-(4-fluorophenyl)-3-pyridylmethyl]-N-[(6-cyano-chroman-2-yl)-methyl]-amine, maleate;

from 2-aminomethyl-5-cyano-chromane and 3-(chloromethyl)-5-(4-fluoro-phenyl)-pyridine N-[5-(4-fluorophenyl)-3pyridylmethyl]-N-[(5-cyano-chroman-2-yl)-methyl]-amine, maleate;

from 2-aminomethyl-5-fluoro-chromane and 3-(chloromethyl)-5-(4-fluoro-phenyl)-pyridine N-[5-(4-fluorophenyl)-3-pyridylmethyl]-N-[(5-fluoro-chroman-2-yl)-methyl]-amine, maleate;

from 2-aminomethyl-6-fluoro-chromane and 3-(chloromethyl)-5-(4-fluoro-phenyl)-pyridine N-[5-(4-fluorophenyl)-3-pyridylmethyl]-N-[(6-fluoro-chroman-2-yl)-methyl]-amine, maleate;

from 2-aminomethyl-chromane and 3-chloromethyl)-5-(3,4-difluoro-phenyl)-pyridine N-[5-(3,4-difluorophenyl)-3-pyridylmethyl]-N-(2-chromanyl-methyl)-amine, maleate, m.p. 175°–177°;

from 2-aminomethyl-chromane and 3-phenoxy-benzylchloride

N-(3-phenoxy-benzyl)-N-(2-chromanyl-methyl)-amine, maleate, m.p. 150°–152°;

from 2-aminomethyl-chromane and 2-(chloromethyl)4-phenyl-pyridine

N-(4-phenyl-2-pyridylmethyl)-N-(2-chromanyl-methyl)-amine, maleate, m.p. 156°–158°;

from 2-aminomethyl-6-bromo-chromane and 3-(chloromethyl )-5-(4-fluoro-phenyl)-pyridine N-[5-(4-fluorophenyl)-3-pyridylmethyl]-N-[2-(6-bromo-(chromanyl)-methyl]-amine, maleate;

from 2-aminomethyl-benzofurane and 3-chloromethyl)-5-(4-fluorophenyl)-pyridine

N-[5-(4-fluorophenyl)-3-pyridylmethyl]-N-(2-benzofurane-methyl)-amine, maleate, m.p. 147°;

from 2-aminomethyl-7-fluoro-chromane and 3-(chloromethyl)-5-(4-fluoro-phenyl)-pyridine N-[5-(4-fluorophenyl)-3-pyridylmethyl]-N-[(7-fluoro-chroman-2-yl)-methyl]-amine, maleate;

from 2-aminomethyl-8-fluoro-chromane and 3-(chloromethyl)-5-(4-fluoro-phenyl)-pyridine N-[5-(4-fluorophenyl)-3-pyridylmethyl]-N-[(8-fluoro-chroman-2-yl)-methyl]-amine, maleate;

from 2-aminomethyl-6-trifluoromethyl-chromane and 3-(chloromethyl)-5-(4-fluorophenyl)-pyridine N-[5-(4-fluorophenyl)-3-pyridylmethyl]-N-[(6-trifluoromethyl-chroman-2-yl)-methyl]-amine, maleate;

from 2-aminomethyl-8-trifluoromethyl-chromane and 3-(chloromethyl)-5-(4-fluorophenyl)-pyridine N-[5-(4-fluorophenyl)-3-pyridylmethyl]-N-[(8-trifluormethyl-chroman-2-yl)-methyl]-amine, maleate.

Example 2

By reaction of 2-aminomethyl-2,3-dihydrobenzofuran with 3-chloro-methyl)-5-(4-fluorophenyl)-pyridine analogously to Example 1, N-[5-(4-fluorophenyl)-3-pyridylmethyl]-N-[(2,3-dihydrobenzofuran-2-yl)-methyl]-amine is obtained, maleate, m.p. 178°–180°.

The following are obtained analogously:

from 2-aminomethyl-2,3-dihydrobenzofuran and 3-(chloromethyl)-5-(4-methoxyphenyl)-pyridine N-[5-(4-methoxyphenyl)-3-pyridylmethyl]-N-[(2,3-dihydro-benzofuran-2-yl)-methyl]-amine, maleate;

from 2-aminomethyl-2,3-dihydrobenzofuran and 3-(chloromethyl)-5-(3,4-dimethoxyphenyl)-pyridine N-[5-(3,4-dimethoxyphenyl)-3-pyridylmethyl]-N[(2,3-dihydro-benzofuran-2-yl)-methyl]-amine, maleate;

from 2-aminomethyl-2,3-dihydrobenzofuran and 3-(chloromethyl)-5-(2,4-dimethoxyphenyl)-pyridine N-[5-(2,4-dimethoxyphenyl)-3-pyridylmethyl]-N-[(2,3-dihydro-benzofuran-2-yl)-methyl]-amine, maleate;

from 2-aminomethyl-2,3-dihydrobenzofuran and 3-(chloromethyl)-5-(3,4,5-trifluorophenyl)-pyridine N-[5-(3,4,5-trifluorophenyl)-3-pyridylmethyl]-N-[(2,3-dihydro-benzofuran-2-yl)-methyl]-amine, maleate;

from 2-aminomethyl-2,3-dihydrobenzofuran and 3-(chloromethyl)-5-(2,3,4,5,6-pentafluorophenyl)-pyridine N-[5-(2,3,4,5,6-pentafluorophenyl)-3-pyridylmethyl]-N-[(2,3-dihydro-benzofuran-2-yl)-methyl]-amine, maleate.

Example 3

A mixture of 2.2 9 3-methyl-phenol, preferably the sodium salt there 5.6 g N-(2-chloroethyl)-N-[5-(4-fluorophenyl)-3-pyridylmethyl]-amine ("A") [obtainable by reaction from phthalimid potassium salt and 5-(4-fluorophenyl)-3-chloromethyl-pyridine, cleavage of the product with hydrazine and subsequent reaction with 1,2-dichloroethane] in 50 ml acetonitrile is stirred for 5 hours at 50° and worked up in the conventional manner.

N-[2-(3-methylphenoxy)-ethyl]-N-[5-(4-fluorophenyl)-3-pyridylmethyl]-amine is obtained. Stirring with 0.5 equivalents of maleic acid in 100 ml ethanol gives the maleate, m.p. 152°–154°.

The following are obtained analogously:
from 2,4-dichlorophenol sodium salt and "A"

N-[2-(2,4-dichlorophenoxy)-ethyl]-N-[5-(4-fluorophenyl)-3-pyridyl-methyl]-amine, maleate, m.p. 148°-150°;

from 3-methoxyphenol sodium salt and "A"

N-[2-(3-methoxyphenoxy)-ethyl]-N-[5-(4-fluorophenyl)-3-pyridyl-methyl]-amine, maleate, m.p. 122°-124°;

from 4-methoxyphenol sodium salt and "A"

N-[2-(4-methoxyphenoxy)-ethyl]-N-[5-(4-fluorophenyl)-3-pyridyl-methyl]-amine, m.p. 94°-96°;

from 3-chlorophenol sodium salt and "A"

N-[2-(3-chlorophenoxy)-ethyl]-N-[5-(4-fluorophenyl)-3-pyridylmethyl]-amine, maleate, m.p. 150°-152°;

from 2-chlorophenol sodium salt and "A"

N-[2-(2-chlorophenoxy)-ethyl]-N-[5-(4-fluorophenyl)-3-pyridylmethyl]-amine, maleate, m.p. 153°-155°;

from 2-methoxyphenol sodium salt and "A"

N-[2-(2-methoxyphenoxy)-ethyl]-N-[5-(4-fluorophenyl)-3-pyridylmethyl]-amine, maleate, m.p. 134°-136°;

from 4-chlorophenol sodium salt and "A"

N-[2-(4-chlorophenoxy)-ethyl]-N-[5-(4-fluorophenyl)-3-pyridylmethyl]-amine, maleate, m.p. 163°-164°;

from 2-ethylphenol sodium salt and "A"

N-[2-(2-ethylphenoxy)ethyl]-N-[5-(4-fluorophenyl)-3-pyridylmethyl]-amine, maleate, m.p. 128°-130°;

from 3-cyanophenol sodium salt and "A"

N-[2-(3-cyanophenol)ethyl)-N-[5-(4-fluorophenyl)-3-pyridylmethyl]-amine, oxalate, m.p. 245° (using oxalic acid in place of maleic acid);

from 4-cyanophenol sodium salt and "A"

N-[2-(4cyanophenol)-ethyl]-N-5-(4-fluorophenyl)-3-pyridylmethyl]-amine, oxalate, m.p. 250°;

from phenol sodium salt and N-[3-phenoxy-benzyl)-amine N-(2-phenoxy-ethyl-N-(3-phenoxy-benzyl)-amine, maleate, m.p. 166°-168°;

from phenol sodium salt and "A"

N-(2-phenoxyethyl)-N-[5-(4-fluorophenyl)-3-pyridylmethyl]-amine, m.p. 84°-86°.

Example 4

By reaction of 2-aminomethyl-6-methoxy-chromane and 3-(chloromethyl)-5-(4-fluorophenyl)-pyridine analogously to Example 1 N-[5-(.4-fluorophenyl)-3-pyridylmethyl]-N-[(6-methoxy-2-chromanyl)-methyl]-amine is obtained. Stirring with hydrochlorid acid gives the dihydrochloride, m.p. 205°-206°.

Example 5

By reaction of 2-aminomethyl-chromane and 3-(chloromethyl)-5-(4-fluorophenyl)-pyridine analogously to Example 1 N-[5-(4-fluorophenyl)-3-pyridylmethyl]-N-(2-chromanyl-methyl)-amine is obtained. Stirring with hydrochloric acid gives the dihydrochloride-hemihydrate, m.p. 210°-213°.

Example 6

A solution of 1.8 g 3-aminomethyl-biphenyl [obtainable by reducing 3-cyano-biphenyl] and 1.6 g 2-chloroethyl-phenylether [obtainable by reaction of sodium-phenolate with dichloroethane] in 200 ml of acetonitrile is stirred for 8 hours at room temperature and worked up in a conventional manner to give N-(3-biphenylmethyl)-N-2-phenoxyethyl-amine. Stirring with 0.5 equivalents of maleic acid in 100 ml ethanol gives the maleate, m.p. 178°-180°.

The following are obtained analogously:

from 3-aminomethyl-4'-fluoro-biphenyl and 2-chloroethyl-phenylether

N-(4'-fluoro-3-biphenylmethyl)-N-2-phenoxyethyl-amine, maleate, m.p. 194°-196°;

from 3-aminomethyl-2',4'-difluoro-biphenyl and 2-chloroethyl-phenylether

N-(2',4'-difluoro-3-biphenylmethyl)-N-2-phenoxyethyl-amine;

from 3-aminomethyl-5-phenylpyridine and 2-chloroethyl-phenylether

N-(5-phenyl-3-pyridylmethyl)-N-2-phenoxyethyl-amine, m.p. 77°-70°;

from 2-aminomethyl-4-(3-thienyl)-thiophen and 2-chloroethyl-phenylether

N-[4-(3-thienyl)-2-thienylmethyl]-N-2-phenoxyethyl-amine, m.p. 96°-98°;

from 2-aminomethyl-4-methyl-thiophen and 2-chloroethyl-phenylether

N-(4-methyl-2-thienylmethyl)-N-2-phenoxyethyl-amine;

from 2-aminomethyl-4-methoxy-thiophen and 2-chloroethyl-phenylether

N-(4-methoxy-2-thienylmethyl)-N-2-phenoxyethyl-amine;

from 2-aminomethyl4-ethyl-thiophen and 2-chloroethyl-phenylether

N-(4-ethyl-2-thienylmethyl)-N-2-phenoxyethyl-amine;

from 2-aminomethyl-4chloro-thiophen and 2-chloroethyl-phenylether

N-(4-chloro-2-thienylmethyl)-N-2-phenoxyethyl-amine;

from 3-aminomethyl-4'-fluoro-biphenyl and 2-chloroethyl-(3-cyano-phenyl)-ether

N-(4'-fluoro-3-biphenylmethyl)-N-2-(3-cyano-phenoxy-ethyl)-amine, maleate, m.p. 158°-160°;

from 3-aminomethyl-biphenyl and 2-chloroethyl-(2-methoxy-phenyl)-ether

N-(3-biphenylmethyl)-N-2-(2-methoxy-phenoxy)-ethyl-amine, m.p. 72°-74°;

from 3-aminomethyl-biphenyl and 2-chloroethyl-2-biphenylyl-ether

N-(3-biphenylmethyl)-N-2-(2-biphenyloxy)-ethylamine, maleate, m.p. 146°-148°;

from 3-aminomethyl-5-(4-fluoro-phenyl)-pyridine and 2-chloroethyl-(2-biphenylyl)-ether N-[5-(4-fluorophenyl-3-pyridylmethyl)]-N-2-(2-biphenyloxy)-ethyl-amine, m.p. 134°-136°;

from 3-aminomethyl-biphenyl and 2-chloroethyl-(2-hydroxyphenyl)-ether

N-(3-biphenylmethyl)-N-2-(2-hydroxyphenoxy)-ethylamine, m.p. 88°-90°;

Example 7

A solution of 1.2 g 2-hydroxy-benzonitril and 2.5 g N-2-chloroethyl-N-(5-phenyl-3-pyridylmethyl)-amine [obtainable by reaction of 2-hydroxyethylamine with 3-chloromethyl-5-phenyl-pyridine and subsequent transformation of the product to the 2-chloroethyl-compound by reaction with PCl$_3$] in 200 ml of acetonitrile is stirred for 5 hours at room temperature and worked up in a conventional manner to give N-[2-(2-cyanophenoxy)-ethyl]-N-(5-phenyl-3-pyridylmethyl)-amine. Stirring with 0.5 equivalenets of oxalic acid in 100 ml ethanol gives the oxalate, m.p. 208°.

The following are obtained analogously:

from 2-chloro-phenol and N-2-chloroethyl-N-(5-phenyl-3-pyridylmethyl)-amine

N-[2-(2-chlorophenoxy)-ethyl]-N-5-phenyl-3-pyridylmethyl)-amine;

from 2-methyl-phenol and N-2-chloroethyl-N-5-phenyl-3-pyridylmethyl)-amine

N-[2-(2-methylphenoxy)-ethyl]-N-(5-phenyl-3-pyridylmethyl)-amine;

from 4-chloro-phenol and N-2-chloroethyl-N-(5-phenyl-3-pyridylmethyl)-amine

N-[2-(4-chlorophenoxy)-ethyl]-N-(5-phenyl-3-pyridylmethyl)-amine;

from 4-cyano-phenol and N-2-chloroethyl-N-(5-phenyl-3-pyridylmethyl)-amine

N-[2-(4-cyanophenoxy)-ethyl]-N-(5-phenyl-3-pyridylmethyl)-amine;

from 3-ethyl-phenol and N-2chloroethyl-N-(5-phenyl-3-pyridylmethyl)-amine

N-[2-(3-ethylphenoxy)-ethyl]-N-(5-phenyl-3-pyridylmethyl)-amine;

from 4-trifluoromethyl-phenol and N-2-chloroethyl-N-(5-phenyl-3-pyridyl-methyl)-amine N-[2-(4-trifluoromethylphenoxy)-ethyl]-N-(5-phenyl-3-pyridylmethyl)-amine;

from 2-bromo-phenol and N-2-chloroethyl-N-(5-phenyl-3-pyridylmethyl)-amine

N-[2-(2-bromophenoxy)-ethyl]-N-(5-phenyl-3-pyridylmethyl)-amine;

from 2-aminomethyl-phenyl and N-2-chloroethyl-N-(5-phenyl-3-pyridylmethyl)-amine N-[2-(2-aminomethylphenoxy)-ethyl]-N-(5-phenyl-3-pyridylmethyl)-amine;

from 4-methoxy-phenol and N-2-chloroethyl-N-(5-phenyl-3-pyridylmethyl)-amine

N-[2-(4-methoxyphenoxy)-ethyl]-N-5-phenyl-3-pyridylmethyl)-amine;

from 3-aminomethyl-phenol and N-2-chloroethyl-N-(5-phenyl-3-pyridylmethyl)-amine N-[2-(3-aminomethylphenoxy)-ethyl]-N-5-phenyl-3-pyridylmethyl)-amine;

from 4-aminomethyl-phenol and N-2-chloroethyl-N-(5-phenyl-3-pyridyl-methyl)-amine N-[2-(4-aminomethylphenoxy)-ethyl]-N-5-phenyl-3-pyridylmethyl)-amine.

Example 8

A mixture of 3.1 g N-[2-(2-cyanophenoxy)-ethyl]-N-(5-phenyl-3-pyridyl-methyl)-amine, 3 g NaOH, 50 ml of water and 40 ml of diethylene glycol monoethyl ether is stirred for 3 hours at a bath temperature of 140°. It is cooled and worked up after a conventional manner, and N-[2-(2-carboxamidophenoxy)-ethyl]-N-(5-phenyl-3-pyridylmethyl)-amine is obtained. Stirring with 0.5 equivalents of oxalic acid in 100 ml ethanol gives the oxalate, m.p. 230°.

Example 9

Analogously to Example 8 N-[2-(4-carboxamidophenoxy)-ethyl]-N-(5-phenyl-3-pyridylmethyl)-amine is obtained by partial hydrolysis of N-[2-(4-cyanophenoxy)-ethyl]-N-(5-phenyl-3-pyridylmethyl)-amine.

Example 10

Starting from N-[2-(4-cyanophenoxy)-ethyl]-N-(5-phenyl-3-pyridylmethyl)-amine analogously to Example 8, boiling for 16 hours and then working up in a conventional manner gives N-[2-(4-carboxyphenoxy)-ethyl]-N-(5-phenyl-3-pyridylmethyl)-amine.

Example 11

Starting from N-[2-(2-cyanophenoxy)-ethyl]-N-(5-phenyl-3-pyridylmethyl)-amine analogously to Example 8, boiling for 16 hours and then working up in a conventional manner gives N-[2-(2-carboxyphenoxy)-ethyl]-N-(5-phenyl-3-pyridylmethyl)-amine.

Example 12

Analogously to Example 7 a solution of 2.3 g sodium phenolate and 2.5 g N-3-chloropropyl-N-[5-(4-fluorophenyl)-3-pyridylmethyl]-amine [obtainable by reaction of 3-hydroxypropylamine with 3-chloromethyl-5-(4-fluorophenyl)-pyridine and subsequent transformation of the product to the 3-chloropropyl-compound by reaction with PCl$_3$] in 200 ml of acetonitrile is stirred for 5 hours at room temperature and worked up in a conventional manner to give N-(3-phenoxy-propyl)-N-[5-(4-fluorophenyl)-3-pyridylmethyl]-amine. Stirring with Q5 equivalents of oxalic acid in 100 ml ethanol/water mixture gives the oxalate-hemihydrate, m.p. 217°.

The following are obtained analogously:

from sodium phenolate and N-4-chlorobutyl-N-[5-(4-fluorophenyl)-3-pyridylmethyl]amine N-(4-phenoxy-butyl)-N-[5-(4-fluorophenyl)-3-pyridylmethyl]-amine, maleate, m.p. 143°;

from sodium phenolate and N-2-chloroisopropyl-N-[5-(4-fluorophenyl)-3-pyridylmethyl]-amine N-(2-phenoxy-isopropyl)-N-[5-4-fluorophenyl)-3-pyridylmethyl]-amine, maleate, m.p. 123°–125°;

from sodium thiophenolate and N-2-chloroethyl-N-[5-(4-fluorophenyl)-3-pyridylmethyl]-amine N-(2-thiophenoxyethyl)-N-[5-(4-fluorophenyl)-3-pyridylmethyl]-amine, oxalate, m.p. 230°;

from sodium thiophenolate and N4-chlorobutyl-N-(5-phenyl-3-pyridyl-methyl-amine

N-(4-thiophenoxy-butyl)-N-(5-phenyl-3-pyridylmethyl)-amine;

from sodium thiophenolate and N-3-chloropropyl-N-(5-phenyl-3-pyridyl-methyl)-amine N-(3-thiophenoxy-propyl)-N-(5-phenyl-3-pyridylmethyl)-amine;

from sodium thiophenolate and N-2-chloroisopropyl-N-(5-phenyl-3-pyridylmethyl)-amine N-(2-thiophenoxy-isopropyl)-N-(5-phenyl-3-pyridylmethyl)amine.

Example 13

According to Example 7 the following are obtained analogously:

from 2-chloro-thiophenol and N-2-chloroethyl-N-(5-phenyl-3-pyridyl-methyl)-amine N-[2-(2-chlorothiophenoxy)-ethyl]-N-(5-phenyl-3-pyridylmethyl)-amine;

from 2-methyl-thiophenol and N-2-chloroethyl-N-(5-phenyl-3-pyridyl-methyl)-amine N-(2-(2-methylchlorothiophenoxy)-ethyl]-N-(5-phenyl-3-pyridyl-methyl)-amine;

from 4-chloro-thiophenol and N-2-chloroethyl-N-(5-phenyl-3-pyridylmethyl)-amine

N-[2-(4chlorothiophenoxy)-ethyl]-N-(5-phenyl-3-pyridylmethyl)-amine;

from 4-cyano-thiophenol and N-2-chloroethyl-N-(5-phenyl-3-pyridylmethyl)-amine

N-[2-(4-cyanothiophenoxy)-ethyl]-N-(5-phenyl-3-pyridylmethyl)-amine;

from 3-ethyl-thiophenol and N-2-chloroethyl-N-(5-phenyl-3-pyridylmethyl)-amine

N-[2-(3-ethylthiophenoxy)-ethyl]-N-(5-phenyl-3-pyridylmethyl)-amine;

from 4-trifluoromethyl-thiophenol and N-2-chloroethyl-N-(5-phenyl-3-pyridylmethyl)-amine N-[2-(4-trifluoromethylthiophenoxy)-ethyl]-N-(5-phenyl-3-pyridylmethyl)-amine;

from 2-bromo-thiophenol and N-2-chloroethyl-N-(5-phenyl-3-pyridylmethyl)-amine

N-[2-(2-bromothiophenoxy)-ethyl]-N-(5-phenyl-3-pyridylmethyl)-amine;

from 2-aminomethyl-thiophenol and N-2-chloroethyl-N-(5-phenyl-3-pyridylmethyl)-amine N-[2-(2-aminomethylthiophenoxy)-ethyl]-N-(5-phenyl-3-pyridylmethyl)-amine;

from 4-methoxy-thiophenol and N-2-chloroethyl-N-(5-phenyl--3-pyridylmethyl)-amine N-[2-(4-methoxythiophenoxy)-ethyl]-N-(5-phenyl-3-pyridylmethyl)-amine;

from 3-aminomethyl-thiophenol and N-2-chloroethyl-N-(5-phenyl-3-pyridylmethyl)-amine N-[2-(3-aminomethylthiophenoxy)-ethyl]-N-(5-phenyl-3-pyridylmethyl)-amine;

from 4-aminomethyl-thiophenol and N-2-chloroethyl-N-(5-phenyl-3-pyridylmethyl)-amine N-[2-(4-aminomethylthiophenoxy)-ethyl]-N-(5-phenyl-3-pyridylmethyl)-amine.

Example 14

A solution of 2.8 g N-[2-(2-methoxyphenoxy)-ethyl]-N-[5-(4-fluorophenyl)-3-pyridylmethyl]-amine [obtainable according to Example 3] and one equivalent 3-chloromethyl-5-(4-fluorophenyl)-pyridine in 125 mil of acetonitrile are stirred for 6 hours at 400 and worked up in a conventional manner to give N-[2-(2-methoxyphenoxy)-ethyl]-N N-bis-[5-(4-fluorophenyl)-3-pyridylmethyl]-amine, m.p. 90°–92°.

The following are obtained analogously by reaction with 3-chloromethyl-5-(4-fluorophenyl)-pyridine:

and N-(4-phenoxy-butyl)-N-(5-phenyl-pyridylmethyl)-amine

N-(4-phenoxy-butyl)-N-(5-phenyl-3-pyridylmethyl)-N-[5-(4-fluorophenyl)-3-pyridylmethyl]-amine;

and N-(2-phenoxy-isopropyl)-N-(5-phenyl-3-pyridylmethyl)-amine

N-(2-phenoxy-isopropyl)-N-(5-phenyl-3-pyridylmethyl)-N-[5-(4-fluorophenyl)-3-pyridylmethyl]-amine;

and N-(2-thiophenoxy-ethyl)-N-(5-phenyl-3-pyridylmethyl)-amine

N-(2-thiophenoxy-ethyl)-N-(5-phenyl-3-pyridylmethyl)-N-[5-(4-fluorophenyl)-3-pyridylmethyl]-amine;

and N-(4-thiophenoxy-butyl)-N-(5-phenyl-3-pyridylmethyl)-amine

N-(4-thiophenoxy-butyl)-N-(5-phenyl-3-pyridylmethyl)-N -[5-(4-fluorophenyl)-3-pyridylmethyl]-amine:

Example 15

Analogously to Example 7 a solution of 2.3 g sodium 1-naphtholate and 2.9 g N-2-chloroethyl-N-[5-(4-fluorophenyl-3-pyridylmethyl)-amine [obtainable by reaction of 2-hydroxyethylamine with 3-chloromethyl-5-(4-fluorophenyl)-pyridine and subsequent transformation of the product to the 2-chloroethyl-compound by reaction with $PCl_3$] in 200 ml of acetonitrile is stirred for 5 hours at room temperature and worked up in a conventional manner to give N-[2(1-naphthyloxy)-ethyl]-N-[5-(4-fluorophenyl)-3-pyridylmethyl]-amine, m.p. 92°–94°.

The following are obtained analogously by reaction of 2-naphtholate with N-2-chloroethyl-N-[5-(4-fluorophenyl-3-pyridylmethyl)-amine:

N[2-(2-naphthoxy)-ethyl]-N-[5-(4-fluorophenyl)-3-pyridyl-methyl]-amine, m.p. 128°–130°;

with N-2-chloroethyl-N-[5-(2,4-difluorophenyl-3-pyridylmethyl)-amine:

N-[2-(2-naphthoxy)-ethyl]-N-[5-(2,4-difluorophenyl)-3-pyridylmethyl]-amine.

Example 16

A solution of 2.1 g N-(2-phenoxy-ethyl)-N-[5-(4-fluorophenyl)-3-pyridylmethyl]-amine [obtainable according to Example 3] in 100 ml THF is treated with 2 ml methyliodide under stirring over a period of 3 hours. Working up in a conventional manner gives N-(2-phenoxy-ethyl)-N-[5-(4-fluorophenyl)-3-pyridylmethyl]-N-methyl-amine, oxalate, m.p. 159°–161°;

The following are obtained analogously by alkylation of the secondary amines:

N-[5-(4-fluorophenyl)-3-pyridylmethyl]-N-(2-chromanyl-methyl)-N-methyl-amine, m.p. 71°;

N-3-biphenylmethyl-N-(2-chromanyl-methyl )-N-methyl-amine.

Example 17

By reaction of N-[5-(4-fluorophenyl)-3-pyridylmethyl]-amine with 1-chloro-3-phenylpropane analogously to Example 1 N-[5-(4-fluorophenyl)-3-pyridylmethyl]-N-(3-phenylpropyl)-amine is obtained, m.p. <50°.

Example 18

Analogously to Example 3 one obtaines by reaction of phenol sodium salt with N-(2-chloroethyl)-N-3-(2-pyridyl)-chloromethyl-benzene N-[3-(2-pyridyl)-phenylmethyl]-N-[2-(phenoxy)-ethyl]-amine, maleate, m.p. 170°;

phenol sodium salt with N-(2-chloroethyl)-N-3-(3-pyridyl)-chloromethyl-benzene

N-[3-(3-pyridyl)-phenylmethyl]-N-[2-(phenoxy)-ethyl]-amine, maleate, m.p. 123°–125°.

Preparation of enantiomeric compounds:

Example 19

A solution of 4.5 g 2-aminomethyl-chromane [obtainable by reacting 3-(2-hydroxy-phenyl)-propanal with KCN and subsequent catalytic reduction of the 2-cyano-chromane] and 3.9 g tosylproline in 190 ml ethanol are refluxed for 15 minutes. Afterwards the solution is cooled down to 5° while it is stirred. During the cooling procedure a few crystalls of pure (R)-2-aminomethyl-chromane were added. The solution was kept under stirring at 50 for a period of 18 hours and afterwards the pure enantiomer (R)-2-aminomethyl-chromane was separated. The crystallisation process was repeated two times with the crystals derived from the first crystallisation in order to yield an enantiomeric excess of more than 99%.

Subsequently the (R)-2-aminomethyl-chromane was reacted with 3-(chloromethyl)-5-(4-fluorophenyl)-pyridine analogously to Example 1 to give (R)-(-)-2-[5-(4-fluorphenyl)-3-pyridyl-methylaminomethyl]-chromane [=(R)-(-)-1 N-(5-(4-fluorophenyl)-3-pyridylmethyl]-N-2-chromanyl-methyl)-amine]. Stirring with 0.1 n hydrochloric acid solution yields the dihydrochloride, m.p. 234°–235°; $[a^{20}]=-65°$ (c=1, methanol).

Analogously by reaction of (S)-2-aminomethyl-chromane and 3-(chloromethyl)-5-(4-fluoro-phenyl)-pyridine (S)-(+)-2-[5-(4-fluorophenyl-3-pyridyl-methylaminomethyl]-chromane [ =(S)-(+)-1 N-[5-(4-fluorophenyl)-3-pyridylmethyl]-N-(2-chromanyl-methyl)-amine] is obtained. Stirring with 0.1 n hydrochloric acid solution yields the dihydrochloride, m.p. 227°–228°, $[a^{20}]=+62°$ (c=1, methanol).

Analogously by reaction of (S)-2-aminomethyl-8-methoxy-chromane and 3-(chloromethyl)-5-(4-fluoro-phenyl)-pyridine: (S)-(+)-2-[5-(4-fluorphenyl)-3-pyridyl-methylaminomethyl]-8-methoxy-chromane [=(S)-(+)-1 N-[5-(4-fluorophenyl)-3-pyridylmethyl]-N-[2-(8-methoxy-chromanyl)-methyl]-amine] is obtained. Stirring with 0.1 n hydrochloric acid solution yields the dihydrochloride, m.p. 214°–215°.

Analogously by reaction of (R)-2-aminomethyl-8-methoxy-chromane and 3-(chloromethyl)-5-(4-fluoro-phenyl)-pyridine: (R)-(-)-2-[5-(4-fluorphenyl)-3-pyridyl-methylaminomethyl]-8-methoxy-chromane [=(R)-(-)-1 N-[5-(4-fluorophenyl)-3-pyridylmethyl]-N-[2-(8-methoxy-chromanyl)-methyl]-amine] is obtained. Stirring with 0.1 n hydrochloric acid solution yields the dihydrochloride, m.p. 214°.

Example 20

A solution of 5 g (R)-2-aminomethyl-chromane [obtainable by reaction of 2-carboxy-chromane and (+)-phenylethylamine, separation of the mainly crystallisating diastereomer purification by recrystallisation from ethanol, transformation into the ethyl chromanate, additional purification via HPLC chiral phases (Chiracel OJ™), transformation into the amide, reduction with LiAlH₄ or Vitride™ in THF to give the (R)-2-aminomethyl-chromane] was reacted with 3-(chloromethyl)-5-phenyl-pyridine analogously to Example 1 to give (R)-(-)-2-[5-phenyl-3-pyridyl-methylaminomethyl]-chromane [=(R)-(-)-1 N-(5-phenyl-3-pyridylmethyl)-N-(2-chromanyl-methyl)-amine]. Stirring with 0.1 n hydrochloric acid solution yields the dihydrochloride, m.p. 243°–244°.

Analogously by reaction of (S)-2-aminomethyl-chromane and 3-(chloromethyl)-5-phenyl-pyridine (S)-(+)-2-(5-phenyl-3-pyridyl-methylaminomethyl)-chromane [=(S)-(+)-1 N-(5-phenyl-3-pyridylmethyl)-N-(2-chromanyl-methyl)-amine] is obtained. Stirring with 0.1 n hydrochloric acid solution yields the dihydrochloride, m.p. 244°–245°.

Analogously by reaction of (S)-2-aminomethyl-8-methoxychromane and 3-(chloromethyl)4'-fluoro-biphenyl:

(S)-(+)-2-[4'-fluor-3-biphenylyl-methylaminomethyl]-8-methoxy-chromane [=(S)-(+)-1 N-[4'-fluoro-3-biphenylyl-methyl]-N-[2-(8-methoxy-chromanyl)-methyl]-amine] is obtained. Stirring with 0.1 n hydrochloric acid solution yields the dihydrochloride, m.p. 189°–190°; $[a^{20}]=+74°$ (c=1, methanol).

Analogously by reaction of (R)-2-aminomethyl-8-methoxy-chromane and 3-(chloromethyl)4'-fluoro-biphenyl:

(R)-(-)-2-[4'-fluor-3-biphenylyl-methylaminomethyl]-8-methoxy-chromane [=(R)-(-)-1 N-[4'-fluoro-3-biphenylyl-methyl]-N-[2-(8-methoxy-chromanyl)-methyl]-amine] is obtained. Stirring with 0.1 n hydrochloric acid solution yields the dihydrochloride, m.p. 189°–190°; $[a^{20}]=-74.3°$ (c=1, methanol).

The examples below relate to pharmaceutical preparations.

Example A: Injection vials

A solution of 100 9 of an active compound of the formula I and 5 g of disodium hydrogenphosphate in 3 l of doubly distilled water is adjusted to pH 6.5 with 2 N hydrochloric acid, sterile filtered, filled into injection vials and lyophilized under sterile conditions, and the vials are closed in a sterile manner. Each injection vial contains 5 mg of active compound.

Example B: Suppositories

A mixture of 20 g of active compound of the formula I is fused with 100 g of soya lecithin and 1400 g of cocoa butter, and the mixture is poured into moulds and allowed to cool. Each suppository contains 20 mg of active compound.

Example C: Solution

A solution of 1 g of active compound of the formula I, 9.38 g of NaH₂PO₄ 2H₂O, 28.48 g of Na₂HPO₄·12H₂O and 0.1 g of benzalkonium chloride is prepared in 940 ml of doubly distilled water. The solution is adjusted to pH 6.8, made up to 1 l and sterilized by irradiation. This solution can be used in the form of eye drops.

Example D: Ointment 500 mg of active compound of the formula I are mixed with 99.5 g of petroleum jell under aseptic conditions.

Example E: Tablets

A mixture of 100 g of an active compound of the formula I, 1 kg of lactose, 600 g of microcrystalline cellulose, 600 g of maize starch, 100 g of polyvinyl-pyrrolidone, 80 g of talc and 10 g of magnesium stearate is pressed to give tablets in a customary manner, such that each tablet contains 10 mg of active compound.

Example F: Coated tablets

Tablets are pressed as stated in Example E and then coated in a customary manner with a coating of sucrose, maize starch, talc, tragecanth and colorant.

Example G: Capsules

Hard gelatin capsules are filled with an active compound of the formula I in the customary manner, so that each capsule contains 5 mg of active compound.

Example H: Inhalation spray 14 g of active compound of the formula I are dissolved in 10 l of isotonic NaCl solution and the solution is filled into commercially available spray containers having a pump mechanism. The solution can be sprayed into the mouth or nose. One spray burst (about 0.1 ml) corresponds to a dose of about 0.14 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I

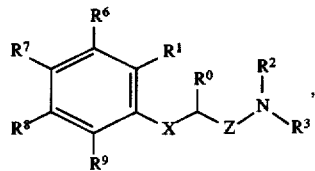

wherein

X is oxygen;

Z is —$(CH_2)_{n1}$—$(CHA)_{n2}$—$(CH_2)_{n3}$—;

n1 is 0, 1, 2 or 3;

n2 is 0 or 1;

n3 is 0, 1, 2 or 3;

n1+n2+n3 is less than 4;

$R^0$ and $R^1$ together are an alkylene chain having 2 C atoms or an alkenylene chain having 2 C atoms;

$R^2$ is H, A, Ac or —$CH_2$—$R^4$;

$R^3$ is —$CH_2$—$R^4$ or —CHA—$R^4$;

$R^4$ is phenyl, 2-, 3- or 4-pyridyl which is, in each case, monosubstituted by $R^5$;

$R^5$ is a phenyl group which is unsubstituted, or mono-, di-, tri-, tetra- or pentasubstituted by F, $CF_3$, A, OA, partial or completely fluorinated A, or combinations thereof;

$R^6$, $R^7$, $R^8$ and $R^9$ are independently of each other H, A, OA, phenoxy, OH, F, Cl, Br, I, CN, $CF_3$, $NO_2$, $NH_2$, NHA, $NA_2$, Ac, Ph, cycloalkyl having 3–7 C atoms, —$CH_2NH_2$, —$CH_2NHA$, —$CH_2NA_2$, —$CH_2NHAc$ or —$CH_2NHSO_2CH_3$;

A is alkyl having 1–6 C atoms;

Ac is alkanoyl having 1–10 C atoms or aroyl having 7–11 C atoms;

Ph is unsubstituted phenyl or phenyl substituted by $R^5$, 2-, 3- or 4-pyridyl or phenoxy; or a physiologically acceptable salt thereof.

2. A compound according to claim 1, wherein said compound is:

(a) N-(5-phenyl-3-pyridylmethyl)-N-2-chromanyl-methylamine or a physiologically acceptable salt thereof;

(b) N-[5-(4-methoxyphenyl)-3-pyridylmethyl]-N-2-chromanyl-methylamine or a physiologically acceptable salt thereof;

(c) N-[5-(4-fluorophenyl)-3-pyridylmethyl]-N-2-chromanyl-methylamine or a physiologically acceptable salt thereof;

(d) N-(4'-fluoro-3-biphenylmethyl)-N-2-chromanyl-methylamine or a physiologically acceptable salt thereof;

(e) N-(3-biphenylmethyl)-N-2-chromanyl-methylamine or a physiologically acceptable salt thereof.

3. A compound according to claim 1, wherein said compound is:

N-[5-(4-fluorophenyl)-3-pyridylmethyl]-N-[(8-methoxy-2-chromanyl)-methyl]-amine or a physiologically acceptable salt thereof.

4. A compound according to claim 1, wherein said is an enantiomer.

5. A compound according to claim 1, wherein Z is methylene and $R^6$, $R^7$, $R^8$ and $R^9$ are each hydrogen.

6. A compound according to claim 1, Z is methylene.

7. A compound according to claim 1, wherein Z is methylene, and $R^4$ is 5-(4-fluorophenyl)-3-pyridyl.

8. A compound according to claim 1, wherein Z is methylene and $R^4$ is 5-phenyl-3-pyridyl.

9. A compound according to claim 1, wherein Z is —$(CH_2)_2$—, —$(CH_2)_3$— or —$(CHCH_3)$— and $R^4$ is 5-(4-fluorophenyl)-3-pyridyl.

10. A compound according to claim 1, wherein,

X is oxygen;

Z is —$CH_2$—, —$(CH)2$—, —$(CH_2)_3$—, —$(CHCH_3)$—, —$CH_2$—$(CHCH_3)$—, —$(CH_2)_2$—$(CHCH_3)$-, —$CH_2$-$(CHCH_3)$—$CH_2$— or —$(CHCH_3)$-$(CH_2)_2$—;

$R^0$ and $R^1$ together are an alkylene or alkenylene chain with 2 C atoms;

$R^2$ is H or A;

$R^3$ is 5-phenyl-3-pyridylmethyl, 5-(fluorophenyl)-3-pyridylmethyl, 5-(methoxyphenyl)-3-pyridylmethyl, 4'-fluoro-3-biphenylmethyl, 3-biphenylmethyl, 2-(q-fluorophenyl)-3-pyridylmethyl, 4-(q-fluorophenyl)-3-pyridylmethyl, 5-(q-fluorophenyl)-3-pyridylmethyl, 6-(q-fluorophenyl)-3-pyridylmethyl, 3-(q-fluorophenyl)-2-pyridylmethyl, 4-(q-fluorophenyl)-2-pyridylmethyl, 5-(q-fluorophenyl)-2-pyridylmethyl, 6-(q-fluorophenyl)-2-pyridylmethyl, 2-(q-fluorophenyl)-4-pyridylmethyl or 3-(q-fluorophenyl)-4-pyridylmethyl, wherein q stands for the prefixes mono-, di-, tri- tetra- or penta-; and $R^6$, $R^7$, $R^8$ and $R^9$ are, in each case independently, H, A, OA, Cl, CN or $CF_3$.

11. A compound according to claim 1, wherein said compound is (R)-(-)-2-[5-(4-fluorophenyl)-3-pyridyl-methylaminomethyl]-chromane.

12. A pharmaceutical composition comprising compound according to claim 1 and a pharmaceutically acceptable carrier.

13. A composition according to claim 12, wherein said composition contains 0.2–500 mg of said compound.

14. A method of treating psychosis or anxiety comprising administering an effective amount of a compound to claim 1.

15. A method according to claim 14, wherein said con administered in an amount of 0.001–10 mg/kg of body weight.

* * * * *